United States Patent [19]

Bradford

[11] Patent Number: Plant 5,455

[45] Date of Patent: Apr. 30, 1985

[54] NECTARINE TREE (SPRING DIAMOND)

[76] Inventor: Norman G. Bradford, 11875 E. Savana Rd., Le Grand, Calif. 95333

[21] Appl. No.: 535,264

[22] Filed: Sep. 23, 1983

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Vergil L. Gerard

[57] ABSTRACT

The present invention relates to a nectarine tree and more particularly to a new and distinct variety broadly characterized by a medium size, vigorous, hardy, productive and regular bearing tree, the fruit of which ripens the last week of June under the ecological conditions described, with the first picking on June 22, 1983. The fruit is freestone, of excellent firmness and has an attractive overall red skin.

1 Drawing Figure

BACKGROUND OF THE VARIETY

The instant variety most nearly resembles the Mike Grand nectarine (U.S. Plant Pat. No. 4,791), but is distinguished therefrom by ripening four days after Mike Grand and an improvement thereon by being somewhat larger in size, having an even, full red color at shipping ripeness, and a smoother skin surface. It is further distinguished by a deep suture which tends to fill out as the fruit ripens, with unequal lips on one side or the other of the fruit.

The instant variety was propogated by me at Bradford Farms in Merced County (San Joaquin Valley), Calif., as the result of open pollination of a second generation seedling from a Red Diamond nectarine seed parent (U.S. Plant Pat. No. 3,165) crossed by an Autumn Free pollen parent (U.S. Plant Pat. No. 2,976). I asexually reproduced the resulting plant by budding and grafting, and such reproduction of plant and fruit characteristics were true to the original plant in all respects.

DRAWING

The accompanying photograph shows the characteristics of the whole fruit in skin color and form, a characteristic fruit divided on its suture plane showing the flesh and stone cavity, and a characteristic stone and leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of eating ripe in the 1983 growing season. All color plate identifications are by reference to Dictionary of Color 1950 (2d ed) by Maerz and Paul.

TREE

General: Hardy, vigorous and dense, of medium spreading and vase shape, with desired shape and density determined by pruning. Very productive and regular bearing.

TRUNK

General: Of medium diameter, grayish-brown shaggy bark; numerous tan lenticles, averaging $\frac{3}{8}''$ in length.

BRANCHES

General: Medium size, medium smooth surface; second year and older growth is grayish-brown in color, newer growth is brown with some green on the ventral side, brown on dorsal side. Numerous medium size, tan lenticles, $\frac{1}{8}''$ to 3/16″ long.

LEAVES

Size: Medium — length, $5\frac{1}{4}''$, width, $1\frac{1}{4}''$.

Form: Lanceolate.

Base: Broadly acute.

Apex: Acutely pointed.

Margin: Crenate.

Veins: Pinnately net veined.

Petiole: Medium — average length, $\frac{3}{8}''$, of medium thickness.

Glands: Averaging two opposite, medium size, reniform, green glands on the petiole and base of leaf.

Stipules: Two per leaf, $\frac{1}{8}''$ long.

Color: Dorsal side Yew Green (24-L-1), ventral side Lincoln Green (23-J-4)

FLOWERS

Buds: Hardy, medium length and circumference, pointed.

Flowers: Large, late blooming compared to other varieties. Pink in color.

FRUIT

Maturity when described: Eating ripe, June 29, 1983.

Size: Uniform, medium size; axial diameter, $2\frac{3}{8}''$, transverse in suture plane, $2\frac{1}{4}''$.

Form: Uniform, symmetrical. Globose to slightly oblong. Longitudinal section elliptical, slightly oblong; transverse through diameter, round with lip on one side.

Suture: A shallow suture extending from base to beyond apex, with slight depression at pistil point.

Ventral surface: Rounded slightly, lipped throughout on one side or the other (but not both) with unequal lips.

Cavity: Rounded with suture showing on both sides. Depth and breadth, $\frac{3}{8}''$. Some minor branch marks.

Base: Truncate.

Apex: Short, truncate.

Pistil point: Very small, some apical and some oblique.

Stem: Length, ¼", width, ⅛".

Skin: General - medium thickness, medium tender. Tenacious to flesh. Tendency to crack is slight.

Skin color: Solid red (Chimney Red 5-L-10).

Flesh:

*Amygdalin.*—Scarce, juice moderate.

*Texture.*—Firm, crisp.

*Fibres.*—Few and fine.

*Ripens.*—Evenly.

*Flavor.*—Subacid.

*Aroma.*—Wanting.

*Eating quality.*—Good.

Flesh color: Yellow (Rattan 11-K-6) to the pit when shipping ripe, occasional red showing when eating ripe.

STONE

Freestone.

Form: Oblong.

Base: Straight.

Hilum: Narrow, oval.

Apex: Mucronate, equal, flattened.

Surface: Irregularly furrowed near apex; ventral edge pitted from base to above center; ridges jagged toward base.

Color: Iran (12-D-7) to India Buff (12-E-5).

Thickness of pit wall: 3/16".

Tendency to split: Slight.

Kernel: Oval form, semi-sweet, viable. Width, ½", length, 13/16", thickness, 3/16". Light yellow pellicle, scant amygdalin.

RESISTANCE TO INSECTS AND DISEASE

Medium resistance to insects and disease.

USE

Local markets, long distance shipping. Excellent keeping quality and shipping quality.

The nectarine tree and its fruit herein described may vary in slight detail due to climatic and soil conditions under which the variety may be grown.

I claim:

1. A new and distinct variety of freestone nectarine tree, substantially as illustrated and described, which most closely resembles Mike Grand (U.S. Plant Pat. No. 4,791) but ripens about four days later and is further distinguished therefrom and an improvement thereon by fruit having a skin which is smoother and has a fuller red color when shipping ripe, and is somewhat larger and firmer when shipping ripe.

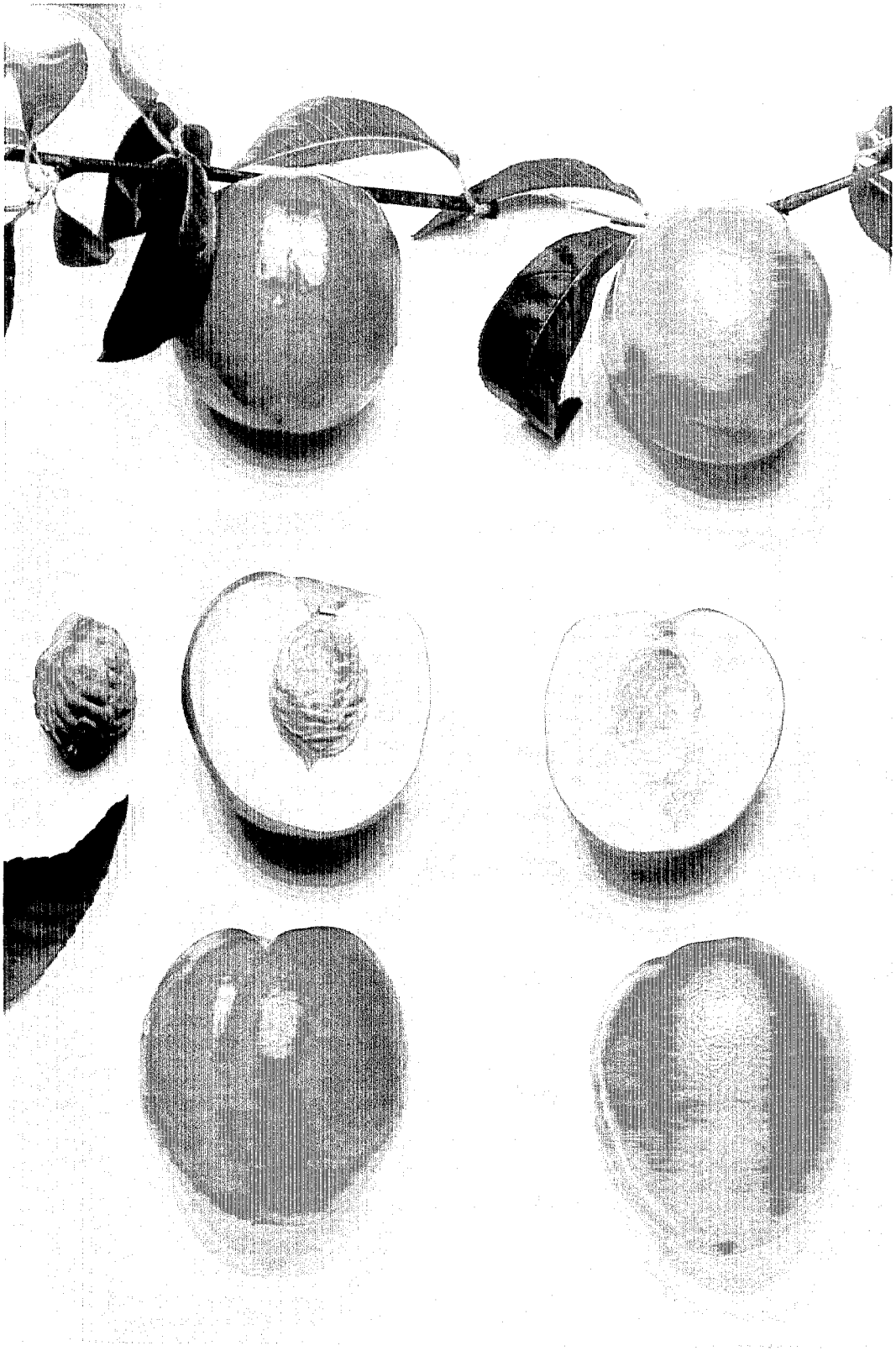

* * * * *